United States Patent
Freud

(10) Patent No.: US 6,178,830 B1
(45) Date of Patent: *Jan. 30, 2001

(54) IN-LINE DILUTING EXTRACTOR

(75) Inventor: Paul J. Freud, Furlong, PA (US)

(73) Assignee: Microtrac, Inc., Montgomeryville, PA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/030,239

(22) Filed: Feb. 25, 1998

(51) Int. Cl.$^7$ ..................................................... G01N 1/20
(52) U.S. Cl. ................................ 73/863.51; 73/863.81; 73/23.31
(58) Field of Search ........................... 73/863.81, 864.33, 73/863.51, 863.02, 863.03, 23.31

(56) References Cited

U.S. PATENT DOCUMENTS

| | | | | |
|---|---|---|---|---|
| 3,803,921 | * | 4/1974 | Dietrich | 73/863.51 |
| 4,385,910 | * | 5/1983 | Eilers et al. | 73/23.31 |
| 4,700,560 | * | 10/1987 | Hoffa et al. | 73/864.83 |
| 5,033,318 | * | 7/1991 | Wendt | 73/863.03 |
| 5,596,154 | * | 1/1997 | Baughman | 73/863.03 |
| 5,753,830 | * | 5/1998 | Sundh | 73/863.81 |

* cited by examiner

Primary Examiner—Daniel S. Larkin
(74) Attorney, Agent, or Firm—Wood, Herron & Evans LLP

(57) ABSTRACT

A device is disclosed that creates and delivers diluted representative samples of a processed medium, flowing as a process stream in a conduit, for the analysis by a particle measurement instrument. The device includes an extraction conduit that includes a probe end extending into the process stream. The probe end includes a pitot-like opening adapted to receive therein a portion of the processed medium. A diluent delivery conduit is housed substantially within and in coaxial alignment with the extraction conduit, forming a sample delivery passage therebetween. The diluent delivery conduit is arranged to emit a stream of diluent into the processed medium entering the probe end creating diluted representative samples of the processed medium. The diluted representative samples flow through the sample delivery passage to a sampling chamber of the particle measurement instrument, where they are analyzed.

3 Claims, 1 Drawing Sheet

IN-LINE DILUTING EXTRACTOR

CROSS-REFERENCE TO RELATED APPLICATIONS

The present application is related to co-pending application, Ser. No. 09/000,463, "A SYSTEM FOR THE IN-LINE EXTRACTION AND DILUTION OF A REPRESENTATIVE SAMPLE OF A PROCESSED MEDIUM", filed on the same date herewith, now abandoned, and having a common assignee to the present invention.

FIELD OF THE INVENTION

This invention relates generally to the field of particle size distribution analysis and more particularly to a device for the in-line extraction and dilution of a representative sample of a processed medium for examination by a particle size distribution measurement instrument.

BACKGROUND OF THE INVENTION

Particle size distribution is an important parameter in many processes and its accurate measurement is required for the precise and cost-effective control of the process. The measurement of particle size distribution in order to accurately control a process finds importance in industries that manufacture cement, cosmetics, pharmaceuticals and the like. A number of instruments are presently used in industry that use angular light scattering or dynamic light scattering techniques to measure particle size distribution in a liquid medium. These instruments analyze and measure the concentration of particles suspended in the liquid medium and provide a measurement that is used to adjust the process in order to correct for any irregularities in the final processed product. One such angular light scattering measurement instrument is taught in U.S. Pat. No. 5,416,580, to Trainer et al, issued May 16, 1995.

In order for these aforementioned instruments to measure correct particle size distribution, an extracted sample representative of the processed medium must be conditioned for measurement. Conditioning disperses the particles within the suspension into a concentration value that is within the concentration requirements of the measurement technique being utilized. The concentration of particles within a typical process is generally higher than is allowed by the measurement technique being utilized and the aforementioned conditioning introduces some form of dilution to disperse the concentration. For example, in the case of instruments that employ angular light scattering techniques, multiple scattering limits the concentration to less than 0.1% of particles in suspension. In the case of dynamic light scattering, particle-to-particle interactions limit concentration to less than 3%. Particle concentrations in a processed medium, however, can be as high as 50% by volume.

One method presently employed that overcomes these limitations is to deliver an extracted sample representative of the processed medium to a conditioning instrument, which works in association with the measurement instrument and dilutes, disperses and finally circulates the conditioned sample to the measurement instrument for analysis. After analysis, the diluted sample is discarded and the cycle repeated. Such conditioning instruments are taught in U.S. Pat. No. 4,496,244, to Ludwig et al, issued Jan. 29, 1985, and U.S. Pat. No. 5,439,288, to Hoffman et al, issued Aug. 8, 1995.

These arrangements have shortcomings in the need to transport a concentrated sample from the process location to the conditioning instrument, the time involved in the conditioning-circulating-flushing cycle and the final discarding of the dilute sample in preparation for the next sample extraction. Such conditioning instruments also suffer from poor reliability and excessive maintenance due inherently to the mechanical actions and motions of the multiple seals, valves, and conduits that are required to extract the sample from the processed medium, condition the extracted sample, and finally deliver the sample to the measurement instrument.

SUMMARY OF THE INVENTION

Therefore, there is provided by the present invention a device for the extraction and delivery of a diluted representative sample of a processed medium flowing in a process stream within a pipe or conduit to a particle measurement instrument for analysis. The device of the present invention includes an extraction conduit that includes a probe end which has an opening extending through an exterior surface of the conduit into an interior cavity. The probe end is arranged to be inserted into a pipe with the opening facing the flow of the process stream.

A diluent delivery conduit connected to a source of diluent medium is substantially housed within the extraction conduit cavity in coaxial alignment with the extraction conduit. A sample delivery passage is formed between the extraction conduit and the diluent delivery conduit. The sample delivery passage connects the device of the present invention to a sampling chamber or cell of a particle measurement instrument. The diluent delivery conduit further includes an opening in direct face-to-face alignment with the extraction conduit opening. Diluent medium flows out of the diluent delivery conduit opening in proximity to said extraction conduit opening.

Responsive to the impact force of the process stream, processed medium enters the extraction conduit opening and mixes with the diluent medium emitted by the diluent delivery conduit opening, thereby forming a stream of diluted processed medium samples. The diluted processed medium samples flow through the sample delivery passage to the sampling chamber of the particle measurement instrument, where they are analyzed.

Accordingly, it is an object of the present invention to provide a diluting and extraction device that delivers to a measurement instrument a conditioned sample representative of the particles present in a processed medium for the real-time, in-situ measurement analysis of the particle size distribution present in the processed medium without the time limitations imposed by the prior art systems.

It is another object of the present invention to provide a diluting and extraction device that requires no mechanical pumping, seals, mixers, gate valves, or mechanically-driven recirculating systems and, therefore, requires a minimal effort to operate and to maintain.

It is still another object of the present invention to provide an effective and simple diluting and extraction device that can be used with any number of particle size distribution measurement instruments to effect the precise and cost-effective control of a processed medium.

BRIEF DESCRIPTION OF THE DRAWINGS

Other objects, features, and advantages of the present invention will be apparent from the following description of a preferred embodiment thereof, taken in conjunction with the single sheet of drawings, in which.

DETAILED DESCRIPTION OF THE INVENTION

Figure 1:
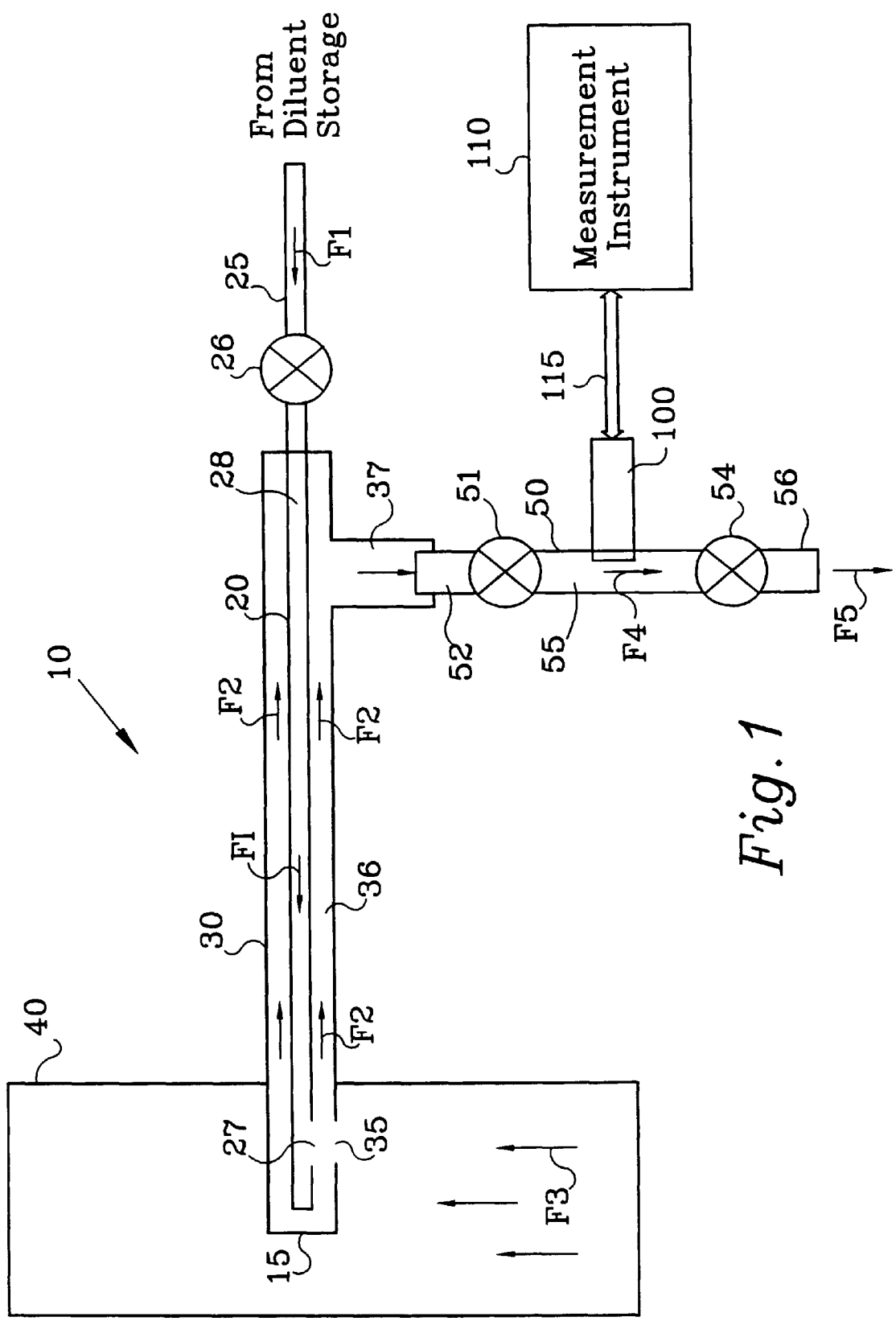
FIG. 1 is a schematic block diagram of the in-line diluting extractor of the present invention for the in-line extraction, dilution and conveyance of a representative sample of a processed medium for examination by a particle size distribution measurement instrument.

Turning to FIG. 1, there is shown the in-line diluting extractor of the present invention that is used to extract, dilute and convey a representative sample of a processed medium to particle measurement instrument. The diluting extractor shown generally at 10, is comprised of a diluent delivery conduit 20 housed within a sample extraction conduit 30, arranged in a coaxial relationship. The diluent delivery conduit 20 is connected to a diluent supply conduit 25. Delivery of a dilution medium to diluent delivery conduit 20 is through a flow control device 26. Flow control device 26 can be a manually adjustable valve, petcock or other such device that can be manipulated to open, close or regulate the flow of diluent flowing through device 26. A dilution medium stored in the diluent storage device (not shown) is conveyed to flow control device 26 via diluent supply conduit 25.

The diluting extractor 10 has a probe end 15 configured in a pitot-like arrangement adapted to be presented into the processed medium to be analyzed. As can be seen in FIG. 1, probe end 15 includes an opening 35 extending from an outer surface of extraction conduit 30 to an inner chamber 36. Similarly diluent delivery conduit 20 includes an opening 27 that is in alignment with opening 35. Opening 27 leads from an outer surface of diluent delivery conduit 20 into an inner chamber 36.

Probe end 15 is arranged to be inserted into a pipe 40 in order to extract representative samples of a processed medium flowing in a process stream within a pipe or conduit 40. Pipe 40 can either be a main conduit that transports the processed medium during a process operation or a by-pass line that shunts a portion of the processed medium from the main conduit. The processed medium flows within pipe 40 as a process stream in the direction shown by flow arrows F3. Probe end 15 is presented into the process stream with the openings 27 and 35 facing flow F3.

Extraction conduit 30 further includes a sample delivery chamber 37 that connects the extraction conduit 30, inner chamber 36, to the fill end 52 of a sampling receptacle 50. Sampling receptacle 50 further includes a fill flow control device 51 located proximate fill end 52. A drain end 56 includes a drain flow control device 54 located proximate drain end 56. Flow control devices 51 and 54 define a sampling chamber or cell 55 therebetween.

A probe 100 is operatively connected via a signal path 115 to a particle measurement instrument 110. The probe 100 is arranged to be inserted into sampling chamber 55. Measurement instrument 110 is a device of the type commonly used in particle size distribution measurement and analysis and that employs angular light scattering or dynamic light scattering techniques to measure particle size distribution. In such instruments a conditioned sample representing the processed medium is deposited in sampling chamber or cell 100, whereby the measurement instrument performs the measurement and analysis on the conditioned sample contained in the sampling chamber. A better understanding of such an instrument and the method used for measurement and analysis may be had by reference to U.S. Pat. No. 5,416,580, to Trainer et al, issued May 16, 1995.

With renewed reference to FIG. 1, an explanation of the operation of extracting a sample of the processed medium will now be given. A processed medium flowing in a process stream through pipe 40, in the direction shown by flow arrows F3, enters opening 35 and into chamber 36. The impact force exerted by the process stream drives a continuous stream of processed medium into chamber 36 which migrates through the extraction conduits inner chamber 36 in the direction shown by flow arrows F2. The processed medium extracted migrates through chamber 36 and is delivered to chamber 37. Opening flow control device 51 allows the entry of processed medium from chamber 37 into sampling chamber 55. The processed medium flows into chamber 55 in the direction shown by flow arrow F4, thereby filling chamber 55. When sampling chamber 55 is filled, flow control device 51 is closed, providing a sample for reading by the measurement instrument probe 100. Upon completion of the measurement, flow control device 54 is opened and the sample is evacuated via drain end 56 in the direction shown by flow arrow F5. The sample flowing from drain end 56 can be either discarded or returned to the process stream of pipe 40, downstream of probe end 15. Flow control device 54 is then closed, preparing sampling chamber 55 for the next sample to be measured.

As it will be understood by those skilled in the art, the arrangement just described illustrates a means of conveying on a demand basis a concentrated sample of the processed medium to the measurement instrument 110 for analysis. However, as was previously explained, in order for the measurement instrument to correctly measure particle size distribution, the representative sample must be conditioned. Conditioning introduces some form of diluent or clear suspending medium fluid to disperse the concentration. The dilution is accomplished by the introduction of a diluent medium to the processed medium before it is driven to the sampling chamber 55.

Returning to FIG. 1, the operation of the diluent delivery and the formulation of a conditioned representative sample of processed medium in accordance to the present invention will now be given. Opening flow control device 26 allows the introduction of a clear diluent medium from a storage device (not shown) to diluent delivery conduit 20. The diluent flows through flow control device 26 in the direction of flow arrow F1 into the inner chamber 28 of diluent delivery conduit 20. Any convenient method for extracting the diluent from the storage device can be employed, including, but not limited to, motor driven pumps or gravity feed. The diluent exits inner chamber 28 at opening 27 and is combined with the processed medium flowing through opening 35, thereby forming a conditioned or diluted representative sample of the processed medium. The now conditioned representative samples being continually formed are driven by the impact force exerted by the process stream flowing in conduit 40 into delivery chamber 37. As was previously explained, opening flow control device 51 allows the conditioned representative samples to enter and fill sampling chamber 55, whereby they can be analyzed by measurement instrument 110 via probe 100. Upon completion of the measurement operation, flow control device 54 is opened, draining chamber 55 in preparation of the next fill operation.

The dilution ratio, that is, the amount of diluent that the representative sample extracted contains, is controlled by balancing the rate of flow of diluent with the flow of processed medium flowing into the extraction conduit 30. The flow rate of processed medium into extraction conduit 30 is a function of the impact force applied to opening 35 by the flow rate F3 of the process stream. The total flow F2 through chamber 36 and into delivery chamber 37 is the sum of the flow rate of F1 and F3. If the diluent flow rate F1 is made large enough, the pressure of the diluent exiting opening 27 can exceed the pressure generated by the flow F3 of the process stream against opening 35. In this situation, diluent will flow into the process stream with no process sample being extracted. At a lower diluent flow rate the pitot pressure at opening 35 will exceed the pressure exerted by the flow of diluent F1 and processed medium will flow through opening 35 and mix with the diluent. Therefore, by adjusting the flow F1 of diluent through device 26, the concentration of the representative sample delivered to the sampling chamber 55 can be controlled. A proper concentration of particles-to-diluent is required for an accurate measurement by measurement instrument 110. By reading the measure of loading or attenuation from the measurement instrument 110, flow control device 26 can be manipulated manually to control the flow of diluent. This manual manipulation of the concentration, however, requires the constant attention of the measurement device output by an operator and the manual adjustment of flow control device 26.

However, the introduction of diluent into the diluent delivery conduit 20 can be effectively automated by connecting the signals representing the loading or attenuation of measurement instrument 100 to a controller device to automatically manipulate and control flow control device 26 in the manner taught by co-pending patent application Ser. No. 09/030,463, "A SYSTEM FOR THE IN-LINE EXTRACTION AND DILUTION OF A REPRESENTATIVE SAMPLE OF A PROCESSED MEDIUM", filed on the same date herewith, now U.S. Pat. No. 6,020,960, and having a common assignee with the present invention and which is hereby incorporated by reference.

The arrangement of the present invention provides an in-line diluting extractor that requires no mechanical pumping, seals, mixing chambers, gate valves or mechanical recirculating systems and, therefore, requires a minimal effort to operate and to maintain. Additionally, the present invention delivers to the measurement instrument a conditioned sample representative of the particles present in a processed medium on a real-time, in-situ basis without the time limitations imposed by the prior art systems. Finally, the conditioning and delivery system of the present invention provides an effective and simple system that can be used with any number of particle size distribution measurement instruments to effect the precise and cost-effective control of a processed medium.

The present invention has been described with particular reference to the preferred embodiments thereof. It will be obvious that various changes and modifications can be made therein without departing from the spirit and scope of the invention as defined in the appended claims.

What is claimed is:

1. A device for the extraction and delivery of diluted representative samples of a processed medium, flowing in a process stream, for the analysis by a particle measurement instrument, said device comprising:

an extraction conduit including a probe end having an opening extending through an exterior surface of said extraction conduit into an interior cavity, said probe end located substantially within and transverse to said process stream with said opening facing the flow of said process stream;

a diluent delivery conduit having an interior bore connected to a source of diluent medium, said diluent delivery conduit substantially housed within said extraction conduit cavity in coaxial alignment with said extraction conduit, forming therebetween a sample delivery passage, said diluent delivery conduit including an opening extending through an exterior surface of said diluent delivery conduit into said bore in direct face-to-face alignment with said extraction conduit opening;

a flow control device connected to said diluent delivery conduit and to said source of diluent medium, said flow control device arranged to be operated to connect said source of diluent medium to said diluent delivery conduit bore and to control the flow rate of diluent medium released through said diluent delivery conduit opening; and an extraction chamber connected to said sample delivery passage and to said particle measurement system, said flow control device operated to release diluent medium from said diluent delivery conduit opening over said extraction conduit opening at a flow rate less than the impact force exerted by said process stream against said extraction conduit opening whereby, responsive to said impact force, a portion of said processed medium enters said extraction conduit opening and mixes with said diluent medium in said sample delivery passage proximate said diluent delivery conduit opening, causing a stream of said diluted representative samples to flow through said sample delivery passage into said extraction chamber for analysis by said particle measurement instrument.

2. The device as claimed in claim 1, wherein said process stream is contained within a conduit.

3. The device as claimed in claim 1, wherein said device further includes a sample receptacle having a fill flow control device on a first end connecting said sample receptacle to said extraction chamber and a drain flow device on a second end forming a sampling chamber therebetween, said particle measurement instrument including a probe extending into said sampling chamber, whereby responsive to the operation of said fill flow control device said diluted representative samples enter said sampling chamber from said extraction chamber and said probe under control of said particle measurement instrument conducts an analysis of said diluted representative samples contained in said sampling chamber and upon termination of the analysis said drain flow control device is operated to empty the diluted representative samples from said sampling chamber.

* * * * *

UNITED STATES PATENT AND TRADEMARK OFFICE
CERTIFICATE OF CORRECTION

PATENT NO. : 6,178,830 B1
DATED : January 30, 2001
INVENTOR(S) : Paul J. Freud

It is certified that error appears in the above-identified patent and that said Letters Patent is hereby corrected as shown below:

Column 1,
Line 6, delete "Ser. No. 09/000,463" and insert -- Ser. No. 09/030,463 --.
Line 10, delete "now abandoned" and insert -- now U.S. Pat. No. 6,020,960 --.

Signed and Sealed this

Twelfth Day of March, 2002

*Attest:*

JAMES E. ROGAN
*Attesting Officer*        *Director of the United States Patent and Trademark Office*